United States Patent [19]
Augier et al.

[11] 4,042,574
[45] Aug. 16, 1977

[54] PURIFICATION OF TUBERCULOPROTEINS

[75] Inventors: Jacques Augier; Solange Augier-Gibory, both of Paris, France

[73] Assignee: Institut Pasteur, Paris, France

[21] Appl. No.: 473,475

[22] Filed: May 28, 1974

[30] Foreign Application Priority Data

May 28, 1973 France .................................. 73.19351

[51] Int. Cl.$^2$ ................................................ C07G 7/00
[52] U.S. Cl. .................................... 260/112 R; 424/92
[58] Field of Search ........................ 424/92; 260/112 R

[56] References Cited
FOREIGN PATENT DOCUMENTS 2,082,266  10/1971  France

OTHER PUBLICATIONS

Chem. Abstracts, vol. 77, 1972, 99652p, Augier.
Chem. Abstracts, vol. 52, 1958, 4114g–4114h, Takeda et al.
Chem. Abstracts, vol. 54, 1960, 25034g–25034i, 25035a, Shindo et al.
Chem. Abstracts, vol. 55, 1961, 22709e–22709f, Yamamura.
Chem. Abstracts, vol. 52, 1958, 11365e–11365h, Bretry et al.
Chem. Abstracts, vol. 61, 1964, 5452d–5452e, Geller.
Ann. Immun. (Inst. Pasteur), 1974, pp. 675–685.
Chem. Abstracts, vol. 20, 1926, 2535–2536, Long & Seibert.
Chem. Abstracts, vol. 22, 1928, 3924, Seibert.
Chem. Abstracts, vol. 28, 1934, 7341 8–9, 7342, 1–2, Appel et al., Clark et al.
Chem. Abstracts, vol. 28, 1934, 7284 4–6, Gough.
Chem. Abstracts, vol. 34, 1940, 7323 7–8, Vasahelyi et al.
Chem. Abstracts, vol. 36, 1942, 1663, 3–5, Seibert et al.
Chem. Abstracts, vol. 46, 1952, 11406f–11406i, 11407a–11407b, Taketani.
Chem. Abstracts, vol. 48, 1954, 8864c–8864e, Takeda et al.

Primary Examiner—Paul R. Michl
Attorney, Agent, or Firm—Sughrue, Rothwell, Mion, Zinn and Macpeak

[57] ABSTRACT

An aqueous solution in a neutral medium of the tuberculoprotein C is subjected to the action of an ionized substance before carrying out three different separation processes which consist in bringing the tuberculoprotein C into solution in water in a proportion of 5% by weight and in neutralizing. The first process consists in adding the ionized substance in an alcohol medium and in carrying out ultracentrifugation for two hours at 40,000 g in order to obtain tuberculoproteins CA in the form of a supernatant liquid. The second process consists in adding a solution of the ionized substance, in carrying out ultrafiltration, concentration and precipitation with trichloroacetic acid in order to obtain the tuberculoprotein CB. The third process consists in adding a solution of the ionized substance then gel-filtering in order to eliminate the molecules having a molecular weight above 200,000 g and in precipitating with trichloroacetic acid in order to obtain a tuberculoprotein CC.

9 Claims, 6 Drawing Figures

PURIFICATION OF TUBERCULOPROTEINS

This invention relates to a novel method of separation of tuberculoproteins.

Tuberculoproteins which are purified protein derivatives are often designated by the initials P.P.D. They are obtained in known manner from tuberculins which are in turn obtained by concentration of filtrates of cultures of tubercle bacilli which have previously been killed by heat. Said tuberculoproteins are employed in order to detect tuberculin allergy for the purpose of diagnosis.

In order to increase the specificity of tuberculoproteins, a number of methods have already been proposed with a view to isolating the active principles of these substances.

In the method described in French patent No. 1,064,634, an initial culture is developed on a synthetic medium of the Sauton type for a period of 8 to 10 weeks and inactivated at 100° C. An organic acid such as benzoic acid is added to the culture filtrate and the pH value is reduced to approximately 3. The resultant precipitate is put in suspension in acetone and the insoluble product thus obtained is a P.P.D. powder known as IP 48.

The method described in French Patent No 2,082,226 consists in starting with P.P.D. IP 48 mentioned above and carrying out a precipitation of tuberculoproteins in an acid medium in the presence of substances which are intended to break the hydrogen bonds, in removing the precipitate which has formed, in precipitating the supernatant liquid by addition of acetone, in putting it back into solution, in adding to the solution a cellulose modified by chemical groups which introduce weakly basic functions and in precipitating by addition of trichloroacetic acid. A so-called tuberculoprotein C is thus obtained.

It has now been discovered that tuberculoprotein C could also be separated into two fractions, one fraction being formed of tuberculoprotein which are very closely aggregated by the presence of ionized substances, the other fraction being formed of tuberculoproteins which are loosely aggregated by the same substances as shown by a study of said fraction on a gel of "Sephadex G200".

The invention is directed to a method of purification of tuberculoproteins in which a precipitation of tuberculoproteins is carried out in an acid medium in the presence of substances which break the hydrogen bonds, the formed precipitate is removed, the supernatant liquid is precipitated by acetone and then redissolved, filtration is carried out through a column of cellulose modified by chemical groups which introduce weakly basic functions and a tuberculoprotein C is precipitated by addition of trichloroacetic acid, said method being characterized in that an aqueous solution in a neutral medium of tuberculoprotein C is subjected to the action of an ionized substance prior to carrying out further separations in accordance with three different processes.

All the ionized substances can be employed and can be as widely different as sodium chloride, sodium dodecyl sulphate and guanidine hydrochlorate, for example. Broadly speaking, it is possible to employ all the mineral or organic ionized substances which do not affect tuberculoprotein C or its solubility.

A first separation process consists in bringing the tuberculoprotein C into solution in water in a proportion of 5 percent by weight, in neutralizing and in adding the ionized substance in an alcohol medium and in carrying out ultracentrifugation for two hours at 40,000 g, which makes it possible to obtain a supernatant liquid consisting of a tuberculoprotein CA.

A second separation process consists in bringing the tuberculoprotein C into solution in water, in neutralizing and adding a solution of the ionized substance, in separating the coarse aggregates from the non-aggregated substances by ultrafiltration. A tuberculoprotein CB is obtained by concentration and precipitation with trichloroacetic acid of the non-aggregatable substances.

A third separation process consists in bringing the tuberculoprotein C into solution in water in a proportion of 3 percent by weight, in neutralizing and in adding an ionized substance, then in filtering through a column consisting of gel beads having a predetermined porosity in order to remove the molecules having a molecular weight above 100,000 (for example by means of Sephadex G200) and in precipitating a tuberculoprotein CC with trichloroacetic acid.

Further characteristics and advantages of the invention will become apparent from the following description which is given with reference to the accompanying drawings, wherein:

FIG. 1 represents the curve obtained in the absence of ionized substances;

FIG. 2 represents the curve obtained in the presence of 1M NaCl;

FIG. 3 represents the curve obtained in the presence of SDS (2%);

FIG. 4 represents the curve obtained in the presence of 6M guanidine hydrochlorate;

FIG. 5 represents the curve obtained in the presence of "Triton X 100" (2%);

Figure 1:
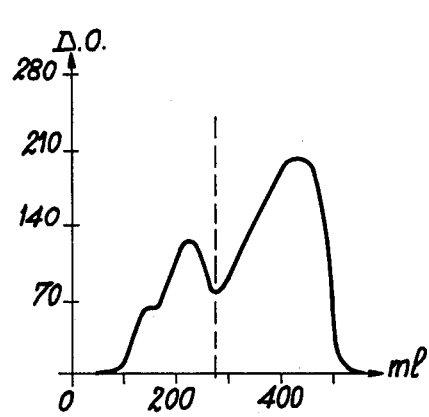
FIGS. 1 to 5 represent the elution curves obtained on Sephadex G200.
Figure 2:
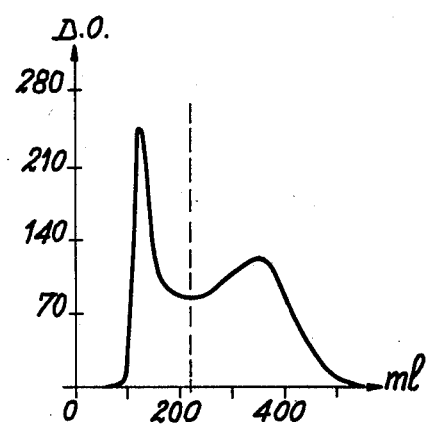
Figure 3:
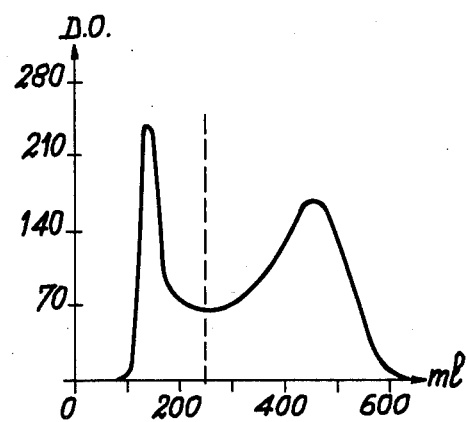
Figure 4:
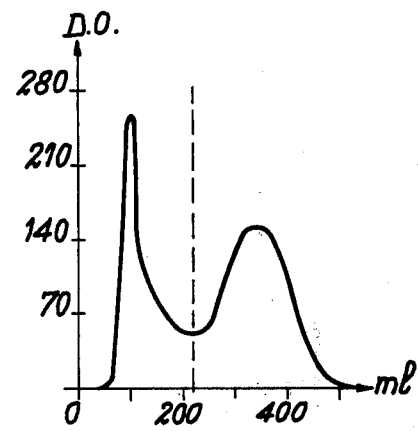
Figure 5:
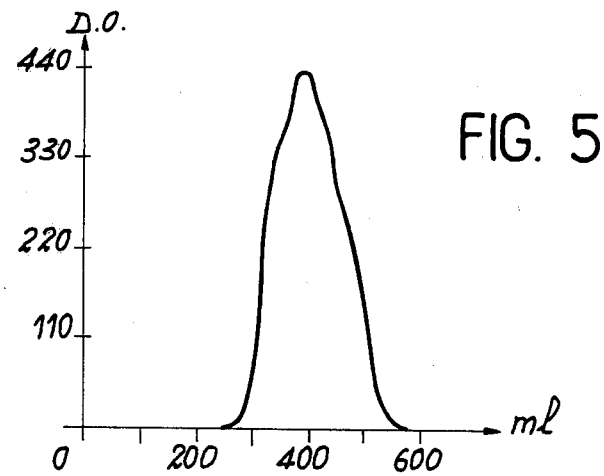

A study of tuberculoprotein C has been carried out by chromatography in a column of Sephadex G200 gel. The protein concentration of the sample introduced into the column was intended to be within the range of 2 to 3.5% and the pH was intended to be in the vicinity of 7. The substances corresponding to the excluded peak are designated as C-L and those corresponding to the included peak are designated as C-1.

Five elution solutions made up of distilled water were employed, namely distilled water alone, sodium chloride 2M, sodium dodecyl sulphate (SDS) in a proportion of 2 percent by weight, 6M guanidine hydrochlorate, "Triton X 100" in a proportion of 2 volume percent, each test was carried out as follows:

200 mg of tuberculoprotein C was dissolved in 6 ml of the selected eluent, the pH was brought to the value of 7 by N sodium hydroxyde. The solution was clarified by centrifugation if necessary. Said sample was introduced into a column having a diameter of 2.5 cm and a length of 90 cm, said column being balanced by the same eluent containing 4 volume percent of primary butyl alcohol as antiseptic.

The protein substances contained in the peak or peaks obtained (as shown in FIGS. 1 to 5) were extracted differently according to the eluent employed. After elution with distilled water or 1M NaCl, the selected fractions were concentrated in vacuo or on a "Diaflo Amicon UM2" membrane, then precipitated with 5 percent of TCA and washed, dried with anhydrous acetone.

In the presence of guanidine, concentration and washing were carried out on a "UM2" membrane followed by precipitation by 5 percent of TCA. In the presence of SDS, concentration was carried out in vacuo followed by precipitation by acetone. After redissolving in distilled water, reprecipitation was carried out in an equal volume of alcohol and acetone. The fraction obtained in the presence of Triton X 100 was concentrated in vacuo and precipitated by 10 volumes of acetone and 10 percent of TCA (calculated with respect to the volume of the solution to be precipitated).

The results of the chemical analyses and of the assays of biological activity are recorded in Table I.

In the presence of distilled water, there was obtained a continuous elution with three peaks. The first two peaks, excluded by the gel, constituted the heavy fraction designated as tuberculoprotein C-L ($H_2O$). The elution volumes corresponding to the summits of these two peaks were respectively 151 ml and 207 ml. The biological activity of both peaks was 31,250 I.U./mg.

The third peak included by the gel represented the light fraction, namely the tuberculoprotein C-1 ($H_2O$) whilst the elution volume corresponding to its summit was 427 ml. Its biological activity was 60,000 I.U./mg.

In the presence of ionizable substances, the elution curve exhibited two summits. In each of the three elution systems, the first peak or excluded peak was designated as C-L and there were therefore present respectively: C-L (NaCl), C-L (guanidine) and C-L (SDS). The elution volumes corresponding to each summit of these peaks were respectively 128 ml, 114 ml and 135 ml. The biological activities attained 24,000 I.U./mg in the case of C-L (NaCl), 28,500 I.U./mg in the case of C-L (guanidine) and 22,000 I.U./mg in the case of C-L (SDS).

The summit of the second included peak corresponded to an elution volume of 361 ml of NaCl, of 340 ml of guanidine, and of 450 ml of SDS.

The biological activities were 67,500 I.U./mg in the case of the tuberculoprotein C-1 (NaCl); 72,500 I.U./mg in the case of the tuberculoprotein C-1 (guanidine) and 57,500 I.U./mg in the case of the tuberculoprotein C-1 (SDS).

In the presence of non-ionizable substances, namely Triton X 100 at 2 volume percent in the case under consideration, the elution curve was reduced to only one included peak. The elution volume corresponding to its summit was 400 ml. After extraction, the tuberculoprotein C-1 Triton X 100 had a biological activity of 60,500 I.U./mg.

These results show that there exists in the tuberculoprotein a low-activity fraction which can be aggregated by ionized substances of widely differing nature and a high-activity fraction which cannot be aggregated by said substances.

An explanatory illustration of the invention is provided by the examples which are given hereinafter without any limitation being implied.

The accompanying Table II is a general schematic representation of the operations involved in the practical application of the method according to the invention.

Table III records the results of chemical analyses and of the activities of the various fractions obtained.

EXAMPLE I

Preparation of the Tuberculoprotein CA 500 mg of tuberculoprotein C were dissolved in 7 ml of distilled water, the pH value having brought to 7 by addition of N sodium hydroxide. There were added 409 mg of sodium chloride, then 3 ml of absolute alcohol. Ultracentrifugation was carried out for 2 hours at 40,000 g.

The supernatant liquid was precipitated by 5 percent by weight of trichloroacetic acid, then centrifuged. The deposit was washed twice with 5% TCA and with anhydrous acetone. By drying in vacuum, 362.5 mg of a powder of tuberculoprotein CA were obtained, namely a yield of 72.5%.

The deposit obtained after ultracentrifugation was placed in 3 ml of distilled water containing one moleculegram of sodium chloride. Centrifugation and extraction with 1M salt water was carried out twice. The supernatant liquid and the two wash solutions were combined in order to be precipitated by TCA and washed with acetone. This heavy fraction having a weight of 122.4 mg was designated as A-L.

EXAMPLE II

Preparation of the Tuberculoprotein CB 500 mg of the tuberculoprotein C were dissolved in 100 ml of an aqueous solution of 1M NaCl in which the pH was brought to a value of 7 by normal sodium hydroxide. Filtration was performed on a commercially available filter known as Diaflo Amicon XM 300 which prevented the passage of molecules having a weight above 300,000 while allowing at least three-fourths of the volume to pass through. The retained solution was washed four times with distilled water containing 1M NaCl, the initial volume being restored at the time of each washing operation while continuing to carry out ultrafiltration. The residue retained on the filter was removed. This operation was not essential and served as a prefiltration for the following operation. The solution was then passed through a filter of a type which is known commercially as "Diaflo Amicon XM 100 A" and which prevented the passage of molecules having a weight exceeding 100,000. The ultrafiltrate was then concentrated on a membrane which prevented the passage of molecules having a molecular weight above 2,000 and known commercially as "Diaflo Amicon UM 2". The fraction retained on "XM 100 A" was washed several times as in the previous case with distilled water containing 1M NaCl and then precipitated by addition of 5% TCA, washed with 5% TCA and finally washed, then dried with anhydrous acetone. There were thus obtained 44.1 mg of a product referred-to as B-L. The fraction which passed through the XM 100 A membrane was concentrated to the maximum extent on a UM 2 membrane, precipitated by addition of 5% TCA, washed twice with 5% TCA and dried with anhydrous acetone. After drying in vacuum, 240 mg of tuberculoprotein CB were thus obtained and represented a yield of 48%.

EXAMPLE III

Preparation of Tuberculoprotein CC 200 mg of tuberculoprotein C were dissolved in 7 ml of an aqueous solution of 1M NaCl, the pH was brought to a value of 7 by addition of normal sodium hydroxide.

Filtration was carried out on a commercially available gel known as Sephadex G200 from which molecules of high molecular weight were excluded. The excluded fraction was designated as C-L and the included fraction was designated as CC. The effluents corresponding to these fractions were treated with 5% TCA after concentration by ultrafiltration on a UM 2 membrane. There were thus obtained 97.2 mg of tuberculoprotein C-L and 110.8 mg of tuberculoprotein CC, namely a yield of 54.4%.

Results of analyses of tuberculoproteins CA, CB and CC a. Tuberculoprotein CA

Chemical analyses relating to the percentage of proteins (P), of polysaccharides (PS) and of deoxyribonucleic acid (DNA) of the two isolated fractions A-L and tuberculoprotein CA are recorded in Table III.

The biological activity of A-L was 20,000 I.U./mg and the biological activity of the tuberculoprotein CA was 40,000 I.U./mg.

b. Tuberculoprotein CB

The chemical analyses of the fractions B-L and tuberculoprotein CB are recorded in Table III.

The biological activity of the fraction B-L was 24,000 I.U./mg and the biological activity of the tuberculoprotein CB was 81,500 I.U./mg.

c. Tuberculoprotein CC

This tuberculoprotein was obtained with a yield of 55.4% by weight. The chemical analyses of the fractions C-L and tuberculoprotein CC are recorded in Table III.

The biological activity of the fraction C-L was 24,000 I.U./mg and the biological activity of the tuberculoprotein CC was 67,500 I.U./mg.

Analyses of the tuberculoproteins CA, CB and CC on Sephadex G 200

The analysis of the tuberculoproteins CA, CB and CC on Sephadex G 200 in the presence of 1M NaCl have shown that the tuberculoprotein CA still contained a fairly high proportion of very readily aggregatable tuberculoproteins, that these latter were present in the tuberculoprotein CB only in negligible quantities and were no longer present at all in the tuberculoprotein CC.

Clinical tests

A tuberculoprotein CB was prepared in a proportion of 10 I.U. per dose in solution in 1.5 wt. % of glycocoll and in 0.05 wt. % of a surfactant which is available commercially under the trade name "Brij 35". This tuberculoprotein was compared with a reference tuberculoprotein of the Staten Serum Institut of Copenhagen, namely RT 23 as prepared in a proportion of 2 T.U. per dose in the presence of "Tween 80" as surfactant. Intradermic injections of these tuberculoproteins were performed on 99 children aged 10 to 15 years in the region of Dakar. There exist in this region a large number of non-specific reactions resulting from disorders caused by atypical bacilli.

Figure 6:
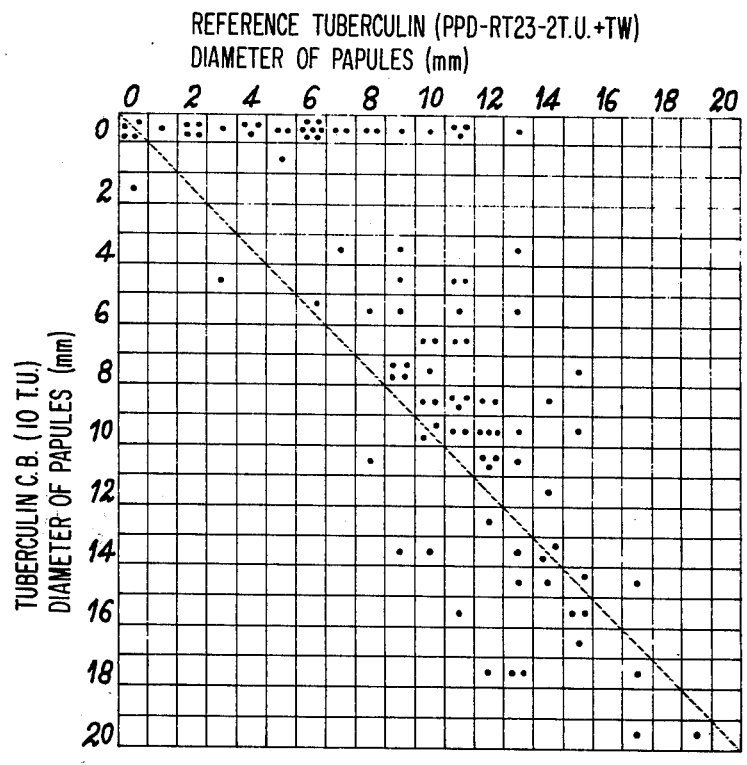
FIG. 6 represents a diagram which shows the specificity of a tuberculoprotein in accordance with the invention.

FIG. 6 represents the diagram of correlation between P.P.D.-CB at 10 I.U. and P.P.D.-RT 23 at 2 T.U. Each point corresponds to one patient. The coordinates correspond to the diameters of the papules obtained in this patient as a result of each P.P.D.

It is apparent that there exist two groups of patients. In a first group, 66 patients have papules which are larger in diameter than 3 mm with both P.P.D.'s. The cloud of measurement points corresponding thereto is distributed in a substantially equal manner on each side of the line of linear regression having a slope of $-1$. In the case of these patients, there is therefore a strong correlation between the two P.P.D.'s.

In a second group, 33 patients exhibit a more or less weak reaction to RT 23. The diameters of the papules extend from 0 to 13 mm with a maximum value of frequency in the vicinity of 6 mm. In the case of P.P.D.-RT 23, this zone corresponds to non-specific reactions. The fact that the same patients are negative with P.P.D.-CB proves that this latter is more specific than P.P.D.-RT 23.

TABLE I

| Weight of the tuberculoprotein C | Name of the tuberculoprotein obtained | Weight and yield of the fraction obtained | Solubility at pH=7 | Chemical analyses % | | | Biological activity IU/mg |
|---|---|---|---|---|---|---|---|
| | | | | Proteins | PS | DNA | |
| 200 mg | C-1 (H₂O) | 144 mg namely 72 % | +++ | 85.5 | 4.6 | 0.6 | 60,000 |
| | C-L (H₂O) | 42.8 mg | ± | 69 | 11.3 | 0 | 31,000 |
| 200 mg | C-1 (NaCl) | 110.8 mg namely 55.4 % | +++ | 80 | 2 | 0.5 | 67,500 |
| | C-L (NaCl) | 97.2 mg | ± | 37.5 | 2.3 | 0 | 24,100 |
| 200 mg | C-1 (guanidine) | 61.5 mg namely 30.7 % | +++ | 90 | 1.7 | 0.4 | 72,500 |
| | C-L (guanidine) | 67.8 mg | ± | 79.5 | 5.6 | 0.5 | 28,500 |
| 200 mg | C-1 (SDS) | 135 mg namely 67.5 % | +++ | 74.5 | 3 | 0.55 | 57,500 |
| | C-L (SDS) | 67.8 mg | ± | 64 | 6.3 | 0 | 22,000 |
| 200 mg | C-1 (Triton X100) | 134.7 mg namely 67.3 % | +++ | 90 | 3.1 | 0 | 60,500 |

TABLE II

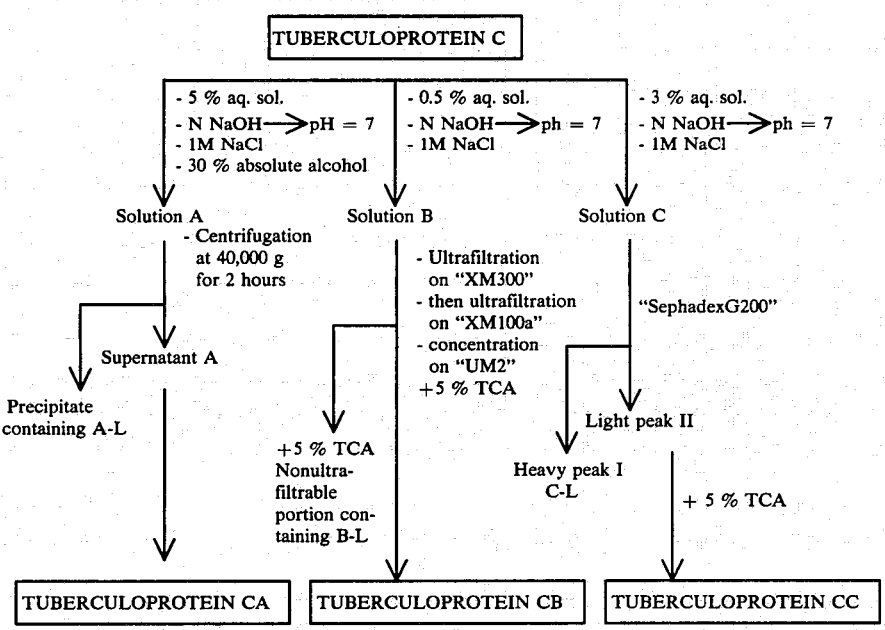

TABLE III

| Examples | Weight of the tuberculo-protein C | Name of the tuberculoprotein obtained | Weight and yield of the fraction obtained | Solubility at pH = 7 | Chemical analyses % | | | Biological activity IU/mg |
|---|---|---|---|---|---|---|---|---|
| | | | | | Proteins | PS | DNA | |
| I | 500 mg | CA | 362.5 mg namely 72.5 % | +++ | 85 | 2.4 | 0.3 | 40,000 |
| | | A-L | 122.4 mg | ± | 69.5 | 4.2 | 0.8 | 20,000 |
| II | 500 mg | CB | 240 mg namely 48 | +++ | 91.5 | 4.3 | 0.5 | 81,500 |
| | | B-L | 41.4 mg | ± | 55 | 1.5 | 2 | 24,000 |
| | | CC the same as C-I (Na Cl) | 110.8 mg namely 55.4 % | +++ | 80 | 2 | 0.5 | 67,500 |
| III | 200 mg | C-L the same as C-L (NaCl) | 97.2 mg | ± | 37.5 | 2.3 | 0 | 24,000 |

What we claim is:

1. A method of purification of tuberculoprotein C in which tuberculoprotein C is prepared by a precipitation of tuberculoproteins carried out in an acid medium in the presence of substances which break the hydrogen bonds, the formed precipitate is removed, the supernatant liquid is precipitated by acetone and then redissolved, filtration is carried out through a column of cellulose modified by chemical groups which introduce weakly basic functions and a tuberculoprotein C is precipitated by addition of trichloroacetic acid, wherein the improvements comprises purifying said tuberculoprotein C by subjecting an aqueous solution thereof in a neutral medium to the action of an ionized mineral or organic substance which does not affect the tuberculoprotein C or the solubility thereof to produce (1) a closely aggregated tuberculoprotein fraction and (2) a loosely and nonaggregated tuberculoprotein fraction; separating said two fractions from one another and recovering said second loosely and non-aggregated fraction.

2. A method according to claim 1, wherein the ionized substance is selected from sodium chloride, sodium dodecylsulphate and guanidine hydrochlorate.

3. A method according to claim 1, wherein said last separation process comprises bringing the tuberculoprotein C into solution in water in a proportion of 5 percent by weight, in neutralizing and in adding the ionized substance in an alcohol medium and in carrying out ultracentrifugation for two hours at 40,000 g in order to obtain a supernatant liquid consisting of tuberculoproteins CA.

4. A method according to claim 1, wherein after subjecting said tuberculoprotein C to the action of the ionized substance, separation is carried out by ultrafiltration to obtain the loosely and non-aggregated fraction in the supernatant liquid, and then concentration and precipitation of the supernatant liquid is carried out with trichloracetic acid in order to obtain said loosely and non-aggregated fraction.

5. A method according to claim 1, wherein said last separation process comprises bringing the tuberculoprotein C into solution in water, in neutralizing and adding a solution of the ionized substance, then in filtering through a gel medium having a porocity in order to remove the molecules having a molecular weight above 100,000g, and in precipitating the filtrate with trichloracetic acid in order to obtain a tuberculoprotein CC.

6. The tuberculoprotein product obtained by the process of claim 1.

7. The tuberculoprotein product obtained by the process of claim 3.

8. The tuberculoprotein product obtained by the process of claim 4.

9. The tuberculoprotein product obtained by the process of claim 5.

* * * * *